United States Patent
Chang et al.

(10) Patent No.: US 8,644,904 B2
(45) Date of Patent: Feb. 4, 2014

(54) DRY ELECTRODE

(75) Inventors: Cheng-Hung Chang, Tainan (TW);
Yi-Shiang Ouyang, Sanchong (TW);
Wen-Ying Chang, Yongkang (TW)

(73) Assignee: Industrial Technology Research Institute, Hsinchu (TW)

( * ) Notice: Subject to any disclaimer, the term of this patent is extended or adjusted under 35 U.S.C. 154(b) by 614 days.

(21) Appl. No.: 12/488,987

(22) Filed: Jun. 22, 2009

(65) Prior Publication Data

US 2010/0185077 A1 Jul. 22, 2010

(30) Foreign Application Priority Data

Jan. 17, 2009 (TW) .............................. 98101850 A

(51) Int. Cl.
*A61B 5/04* (2006.01)
*A61N 1/00* (2006.01)

(52) U.S. Cl.
USPC ........... 600/382; 600/372; 600/386; 600/393; 607/149; 607/152

(58) Field of Classification Search
USPC ................. 600/372, 382, 384, 386, 395–396, 600/389–393; 607/116, 149, 152
See application file for complete search history.

(56) References Cited

U.S. PATENT DOCUMENTS

| | | | |
|---|---|---|---|
| 3,989,036 A * | 11/1976 | Sasamori | 600/396 |
| 4,887,614 A * | 12/1989 | Shirakami et al. | 607/100 |
| 4,967,038 A | 10/1990 | Gevins et al. | |
| 5,511,548 A | 4/1996 | Riazzi et al. | |
| 5,678,545 A * | 10/1997 | Stratbucker | 600/393 |
| 5,746,207 A | 5/1998 | McLaughlin et al. | |
| 6,510,333 B1 * | 1/2003 | Licata et al. | 600/383 |
| 6,622,035 B1 | 9/2003 | Merilainen et al. | |
| 6,835,184 B1 | 12/2004 | Sage et al. | |
| 7,146,221 B2 * | 12/2006 | Krulevitch et al. | 607/116 |
| 7,286,864 B1 * | 10/2007 | Schmidt et al. | 600/372 |
| 2002/0187556 A1 * | 12/2002 | Shartle et al. | 436/149 |
| 2003/0208248 A1 | 11/2003 | Carter et al. | |
| 2004/0073104 A1 | 4/2004 | Brun del Re et al. | 600/372 |
| 2006/0173523 A1 * | 8/2006 | Rainey et al. | 607/152 |
| 2007/0015984 A1 * | 1/2007 | Yeo et al. | 600/372 |
| 2008/0009763 A1 | 1/2008 | Chiou et al. | 600/544 |
| 2009/0137892 A1 * | 5/2009 | Leftly et al. | 600/390 |

FOREIGN PATENT DOCUMENTS

| | | |
|---|---|---|
| TW | M292362 | 6/2006 |
| TW | 200701947 | 1/2007 |

* cited by examiner

*Primary Examiner* — Linda Dvorak
*Assistant Examiner* — Brian M Antiskay
(74) *Attorney, Agent, or Firm* — Allen, Dyer, Doppelt, Milbrath & Gilchrist, P.A

(57) ABSTRACT

A flexible dry electrode and the manufacturing method thereof are provided. The electrode has an electroplated uneven surface and at least one hole and is made of porous material.

13 Claims, 6 Drawing Sheets

DRY ELECTRODE

TECHNICAL FIELD

The disclosure relates to a dry electrode and the manufacturing method thereof, and more particularly to a porous electrode having an uneven surface and the manufacturing method thereof.

BACKGROUND

The US Patent Appl. Pub. No. 2008/0009763 provides a fixable microprobe array which is able to be inserted into the skin and has a conductive layer thereon for sensing a signal.

The TW Patent Appl. Pub. No. 200701947 provides a cloth for detecting the electric signal on the human skin, wherein the cloth is made of metal fibers or conductively polymeric fibers.

The US Patent Appl. Pub. No. 2004/0073104 provides an electrode being applied to measure the physiological signal. By setting a wet foam rubber between the electrode and the skin, the electric conductivity of the electrode is increased and the interferences of the measured signal are decreased.

Keeping the drawbacks of the prior arts in mind, and employing researches full-heartily and persistently, the applicant finally conceived a dry electrode having a relatively lower resistance and the manufacturing method thereof.

SUMMARY

The disclosure provides a dry electrode. The dry electrode comprises a first surface having an uneven structure contacting a target surface and collecting an electric signal from the target surface; a conductive layer embedded thereinto; and a second surface being opposite to the first surface; wherein the dry electrode is made of a porous material.

The disclosure provides a method for manufacturing an electrode. The method comprises the steps of providing a conductive material; impressing and polymerizing the conductive material; forming an uneven surface on the conductive material; etching the conductive material; and forming an electroplate on the conductive material to form the electrode.

DETAILED DESCRIPTION

In order to further illustrate the techniques, methods and efficiencies used to procure the aims of this disclosure, please see the following detailed description. It is believable that the features and characteristics of this disclosure can be understood by the descriptions. It is to be noted that the following descriptions of preferred embodiments of this disclosure are presented herein for the purposes of illustration and description only; it is not intended to be exhaustive or to be limited to the precise form disclosed.

Figure 1A:
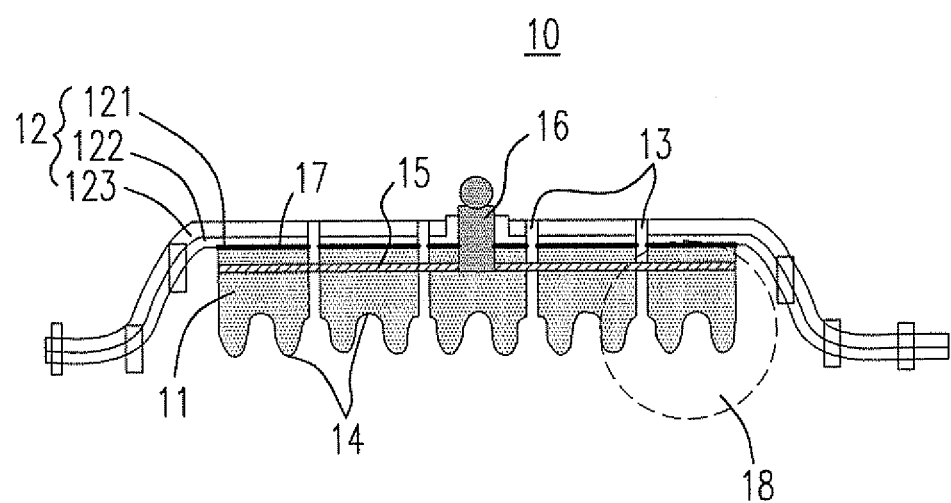
FIG. 1(A) is a schematic diagram according to an embodiment of the present dry electrode 10.

Please refer to FIG. 1(A), which is a schematic diagram showing an embodiment of the dry electrode 10. Dry electrode 10 comprises an main layer 11, a fixing unit 12 and a through hole 13. Main layer 11 has a first surface 14, a conductive layer 15, a connector 16 and a second surface 17. Fixing unit 12 has a cohering layer 121, an insulating layer 122 and an isolating layer 123. Dry electrode 10 is manufacturing by a micro process, where first surface 14 has an uneven structure contacting with a target surface such as a skin. Conductive layer 15 is embedded into main layer 11 and collects and transmits an signal capturing from the target surface, and conductive layer 15 further couples to connector 16 so that the signal is output from connector 16. Fixing unit 12 is applied to fix electrode 10 to the target surface and further provides an electrical isolation for electrode 10. Specifically, cohering layer 121 provides a mechanically cohering strength to fix the electrode 10, and insulating layer 122 and isolating layer 123 respectively provides an insulation and a faraday shield for electrode 10. Those layers of fixing unit 12 can be optionally removed or added thereinto another layer(s) depending on the requirements. Fixing unit 12 is generally posited above second surface 17, but the position of fixing unit 12 can also be configured at any appropriate site of dry electrode 10 based on the requirements. Through hole 13 is penetrating the main layer 11, and applied to increase the ventilation of dry electrode 10.

The uneven structure of first surface 14 is used to increase the contact area between the target surface and the main layer 11. Main layer 11 is made of a soft, porous or vesicant conductive material, and those flexible conductive materials, e.g. the flexible conductive plastic, would further increase the effective area to lower an impedance between main layer 11 and the target surface. In addition, the porous conductive material would increase the ventilation of dry electrode 10 and adjust the moisture between main layer 11 and the target surface.

Specifically, the raw material of main layer 11 can be a conductive polymeric material such as a compositive conductive material, a structural conductive material and flexible porous conductive plastic. The compositive conductive material can be selected from one of a carbon black, a metal power, a metal piece, a metal fiber, a carbon fiber and a combination thereof, and the structural conductive material can be selected form one of a polyacetylene, a polypyrrole, a polyphenylene sulfide, a poly(phthalocyanine) compound, a polyaniline, a polythiophene and a combination thereof.

Either the material and the form of conductive layer 15 is unlimited. For example, conductive layer 15 can be a metal network for matching the flexibility of main layer 1.

The respective materials of first surface 14 and second surface 17 of main layer 11 of the present embodiment are identical, and conductive layer 15 is embedded into main layer 11. However, the respective materials of first surface 14 and second surface 17 can be different from each other by requirements, where the material of first surface 14 is preferably a flexible one.

As shown in FIG. 1(A), connector 16 is coupled to conductive layer 15 and configured on fixing unit 12 and second surface 17 to output the electric signal to an external device. However, connector 16 can also be configured at any appropriate site of dry electrode 10 based on the requirements.

Figure 1B:
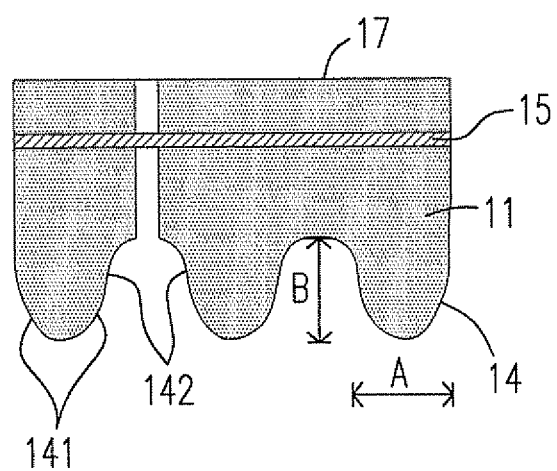
FIG. 1(B) is a schematic diagram showing an amplifying view of scope 18 of FIG. 1(A).

Please refer to FIG. 1(B), which is a schematic diagram showing an amplifying view of scope 18 of FIG. 1(A) and where the relative positions among main layer 11, first surface 14, conductive layer 15 and second surface 17 are clearly illustrated. As shown in FIG. 1(B), the uneven structure of first surface 14 further comprises a plurality of protrusions 141 and a plurality of concavities 142, each of the plurality of protrusions 141 has a width A, each of the plurality of concavities has a depth B, and width A and depth B have a range from 100 um to 1000 um. If main layer 11 is made of the flexible porous material, where the sizes of pores of the flexible porous material are ranged from 10 um to 100 um.

Through the porosity of main layer 11, the uneven structure of first surface 14 would absorb the moisture of the target surface to make main layer 11 to be under a moist surrounding in microcosmic view, by which the resistance between first surface 14 and the target surface is lowered. Moreover, first surface 14 can be electroplated thereon an electroplate, e.g. an electroplating layer, for further lowering the resistance. For example, first surface 14 can be electroplated with a sliver/silver chloride electroplating layer. By coordinating with the moist surrounding, main layer 11 having the sliver/silver chloride-electroplated first surface 14 would have a high electric conductivity and a very low impedance and can be seen as a sliver/silver chloride electrode although main layer 11 is essentially a dry electrode.

The material of electroplating layer can be, for example, a silver, a chlorine silver, a gold, a titanium, a platinum, a stainless steel, an alumni oxide, a carbon, a carbon fiber, a carbon nanotube, a graphite, a diamond, a material being able to lower the impedance or a combination thereof.

Figure 1C:
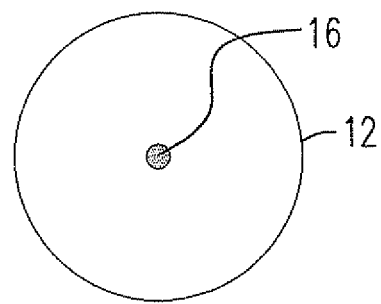
FIG. 1(C) is a schematic diagram of electrode 10 in overlooking view.

Please refer to FIG. 1(C), which is a schematic diagram of dry electrode 10 in overlooking view. As shown in FIG. 1(C), connector 16 is passed through fixing unit 12 and connects to an external device by a direct connection, an electrical connection or a wireless connection. Moreover, a plurality of dry electrodes 10 are able to connect with one another and/or to the measuring or recording devices, where all the mentioned elements can be configured with a portable carrier for a long-term and continuous record of physiological signals from various parts of a user. For a comfortable and long-term use, the fixing unit 12 is preferably made of a soft and ventilative material.

Figure 2A:
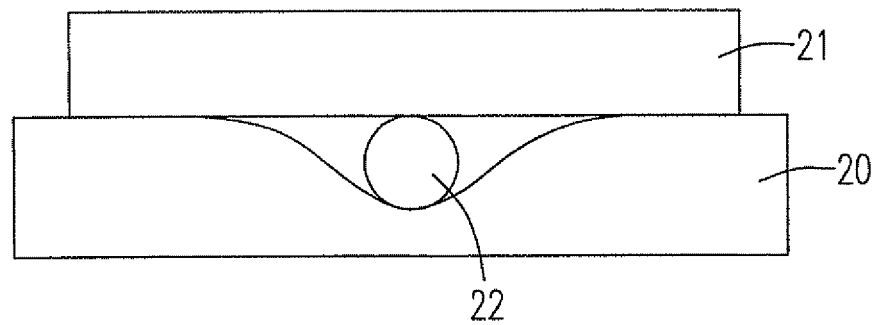
FIG. 2(A) shows a situation that a known hard electrode 21 covers on a skin 20.
Figure 2B:
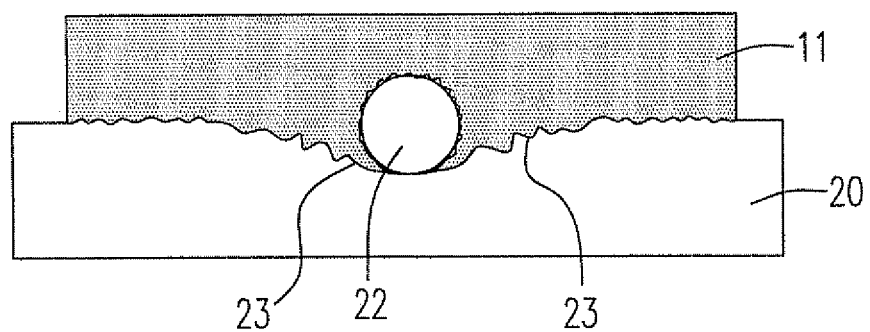
FIG. 2(B) shows a situation that electrode 10 covers on skin 20.

Please refer to FIGS. 2(A) and 2(B), where FIG. 2(A) shows a situation that a known hard electrode 21 covers on a skin 20, and FIG. 2(B) shows a situation that main layer 11 having the uneven structure covers on skin 20. As shown in FIG. 2(A), hard electrode 21 covered on skin 20 cannot correspondingly transform if it meets some protrusions on skin 20 such as a hair 22. Accordingly, hard electrode 21 would fail to closely fit on skin 20 but remain gaps therebetween, by which the effective area of hard electrode 21 is decreased and the impedance/resistance of hard electrode 21 is increased.

On the contrary, as shown in FIG. 2(B), if main layer 11 is covered on the skin, main layer 11 would fit on skin 20 and hair 22 to form a close interface since its uneven surface and flexibility. Apparently, the effective area of main layer 11 is relatively large and the impedance/resistance thereof is relatively low.

Figure 3:
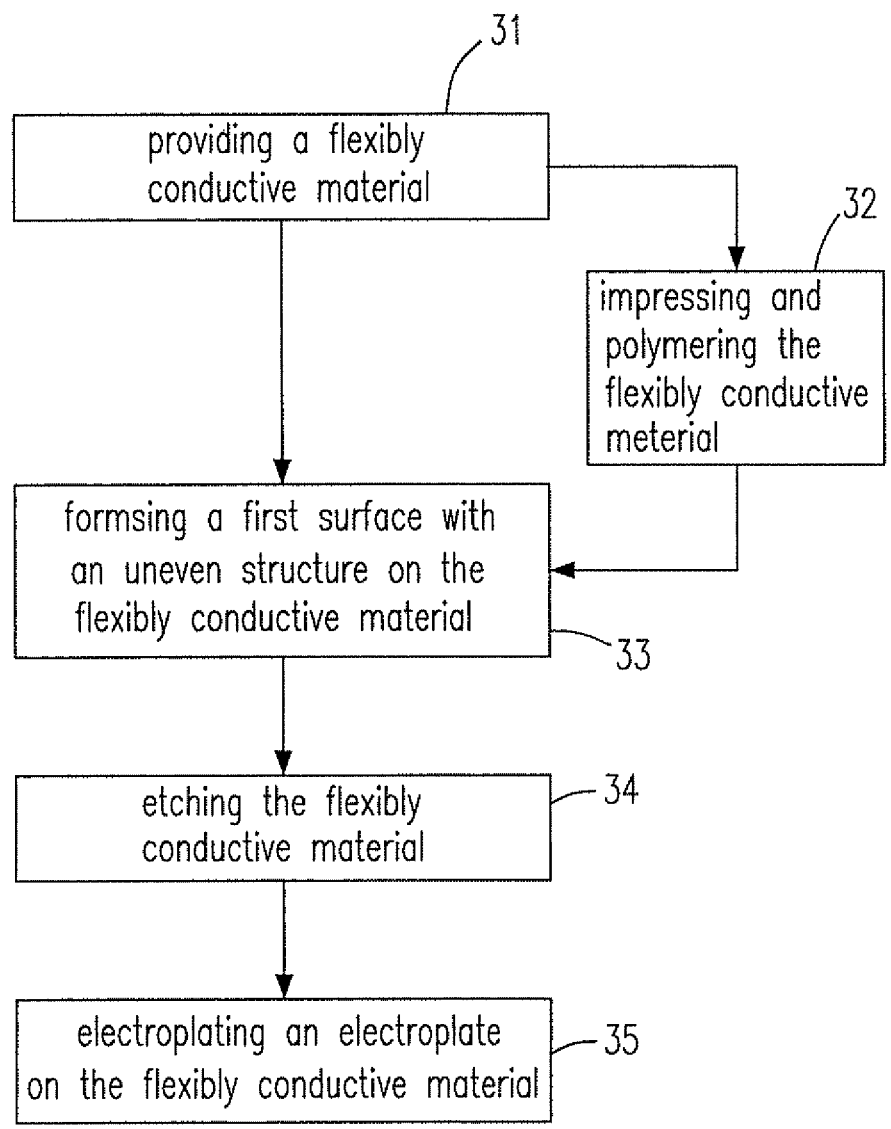
FIG. 3 is a flow chart showing a method for manufacturing the present dry electrode.

Please refer to FIG. 3, which is a flow chart showing a method for manufacturing the present dry electrode 10. As to the method, first, a flexible conductive material is provided (Step 31), wherein the flexible conductive material is any kind of material being applicable to be the electrode, or comprises a polymer, a conductive element and a vesicant. By impressing and polymerizing the flexible conductive material (Step 32), a first surface with an uneven structure, e.g. a wave structure, is formed on the flexible conductive material (Step 33). An etching process (Step 34) is subsequently treated on the flexible conductive material. Then, the flexible conductive material is treated with an electroplating process (Step 35) to form thereon an electroplate, e.g. an electroplating layer, and the flexible dry electrode is formed accordingly.

The Step 32 in the FIG. 3 is performed by a micro process. However, Step 32 is a selective step. According to the characters of the provided flexible conductive material, the uneven surface/structure can be formed by other appropriate processes rather than Step 32, which means Step 32 is bypassed at this situation.

The etching process performed in Step 34 is a reactive ion etching (RIE) process or can be any appropriate one. The material of the electroplate formed in Step 34 is also selected form the candidates of electroplating layer of first surface 14.

An additional step, embedding a conductive layer into the flexible conductive material, can be added into those steps shown in FIG. 3. The conductive layer is applied to collect and transmit the sensed signals form a target region of the target surface. The conductive layer is able to configured with a connector to output the sensed signals to the medical device or the recorder.

The dry electrode formed by processed shown in FIG. 3 can further be configured with a fixing unit or a through hole to increase the applicability and the function thereof. Furthermore, all the mentioned steps can be merged into a roll-to-roll process to produce the present dry electrode fast and greatly.

While the disclosure has been described in terms of what are presently considered to be the most practical and preferred embodiments, it is to be understood that the disclosure need not be limited to the disclosed embodiment. On the contrary, it is intended to cover various modifications and similar arrangements included within the spirit and scope of the appended claims, which are to be accorded with the broadest interpretation so as to encompass all such modifications and similar structures. Therefore, the above description and illustration should not be taken as limiting the scope of the disclosure which is defined by the appended claims.

What is claimed is:

1. A dry electrode, comprising:
    a main layer comprising a flexible material divided into a plurality of spaced apart sections, with adjacent sections separated from one another by a through hole, with each section of the main layer having: a first uneven surface with a plurality of protrusions and at least one concavity therebetween, and a second surface opposite the first uneven surface;
    a conductive layer embedded in the main layer and extending through the plurality of spaced apart sections and the through holes; and
    a fixing unit connected to the second surface of the main layer.

2. A dry electrode according to claim 1, each of the plurality of protrusions has a width, each of the plurality of concavities has a depth, and the width and the depth have a range from 100 um to 1000 um.

3. A dry electrode according to claim 1, wherein the flexible material is a conductive polymeric material being one selected from a group consisting of a compositive conductive material, a structural conductive material and a combination thereof.

4. A dry electrode according to claim 3, wherein the compositive conductive material is one selected from a group consisting of a carbon black, a metal powder, a metal piece, a metal fiber, a carbon fiber and a combination thereof.

5. A dry electrode according to claim 3, wherein the structural conductive material is one selected from a group consisting of a polyacetylene, a polypyrrole, a polyphenylene sulfide, a poly (phthalocyanine) compound, a polyaniline, a polythiophene and a combination thereof.

6. A dry electrode according to claim 1, wherein the main layer is made of a flexible conductive porous plastic.

7. A dry electrode according to claim 1, wherein the dry electrode further comprises an electroplating layer coated on the first uneven surface and made of a material being one selected from a group consisting of a silver, a chlorine silver, a gold, a titanium, a platinum, a stainless steel, an alumni oxide, a carbon, a carbon fiber, a carbon nanotube, a graphite, a diamond and a combination thereof.

8. A dry electrode according to claim 1 further comprising a connector electrically coupled to the conductive layer, and outputting an electric signal.

9. A dry electrode according to claim 1, wherein the fixing unit covers the main layer and comprises a cohering layer, an insulating layer and an isolating layer, the cohering layer provides a mechanically cohering strength for fixing the dry electrode on a target surface when the dry electrode is used, the insulating layer provides an insulation for the dry electrode, and the isolating layer provides a faraday shield for the dry electrode.

10. A dry electrode according to claim 1, wherein at least one of the through hole penetrating holes penetrates the main layer.

11. A dry electrode, comprising:
a main body having an uneven surface with a plurality of protrusions and a plurality of concavities, a through hole disposed in at least one of the plurality of concavities and a second surface opposite the uneven surface, and being made of a flexible material; and
a conductive element embedded into the main body.

12. A dry electrode according to claim 11, wherein the main body is formed of a porous material.

13. A dry electrode according to claim 11, wherein the through hole penetrates the main body and the second surface is opposite to the first uneven surface.

* * * * *